United States Patent
Kim et al.

(10) Patent No.: US 7,452,615 B2
(45) Date of Patent: Nov. 18, 2008

(54) CARBAZOLE DERIVATIVE AND ORGANIC LIGHT EMITTING DEVICE USING SAME

(75) Inventors: Kong Kyeom Kim, Yuseong-gu (KR); Jun Gi Jang, Yuseong-gu (KR)

(73) Assignee: LG Chem, Ltd., Seoul (KR)

( * ) Notice: Subject to any disclaimer, the term of this patent is extended or adjusted under 35 U.S.C. 154(b) by 484 days.

(21) Appl. No.: 11/229,093

(22) Filed: Sep. 19, 2005

(65) Prior Publication Data
US 2006/0063037 A1    Mar. 23, 2006

(30) Foreign Application Priority Data
Sep. 20, 2004    (KR) .................. 10-2004-0074920

(51) Int. Cl.
H01L 51/50    (2006.01)
C09B 5/00    (2006.01)
(52) U.S. Cl. .................. 428/690; 428/917; 313/504; 313/506; 548/416; 549/41; 549/456
(58) Field of Classification Search .................. 428/690, 428/917; 313/504, 506; 548/416; 549/41, 549/456
See application file for complete search history.

(56) References Cited

U.S. PATENT DOCUMENTS

| | | |
|---|---|---|
| 6,461,747 B1 | 10/2002 | Okada et al. |
| 6,537,687 B1 | 3/2003 | Nii |
| 6,555,959 B1 | 4/2003 | Nii |
| 6,649,722 B2 | 11/2003 | Rosenzweig et al. |
| 6,693,295 B2 | 2/2004 | Nii |

FOREIGN PATENT DOCUMENTS

| | | |
|---|---|---|
| JP | 2001-261680 | 9/2001 |
| JP | 2004-055240 | 2/2004 |
| JP | 2004-123619 | 4/2004 |

OTHER PUBLICATIONS

Eklund, et al, "Synthesis of 2.2'-Biindolyls By Coupling Reactions"; *Tetrahedron* 1980, 36, 1439.
Manini, et al, "Acid-Promoted Competing Pathways in the Oxidative Polymerization of 5, 6-Dihydroxyindoles and Related Compounds; Straightforward Cyclotrimerization Routes to Diindolocarbazole Derivatives"; *J. Org. Chem.* 1998, 63, 7002-7008.
Tang, et al."Organic Electroluminescent Diodes" *Appl. Phys. Lett.* 51 (121) Sep. 1987.
Lee, et al. "Facile Synthesis of 4-Alkyl (and Aryl)-2aryl-6-diazo-4H-thieno[3,2-b] pyridine-5,7-diones" J. Org. Chem 2004. 69, 4867-4869 (2004).
Kohra, et al. "Reaction of a-Oxoketene Dithioacetals with Arylamines in the Presensce of $BF_3$-$Oet_2$ for the Synthesis of Ketene S/N-Acetals" Chem. Pharm. Bull. 41(7) 1293-1296 (1993).

*Primary Examiner*—Dawn Garrett
(74) *Attorney, Agent, or Firm*—McKenna Long & Aldridge LLP

(57) ABSTRACT

Disclosed is a compound of Formula 1 and an organic light emitting device using the same.

Formula 1

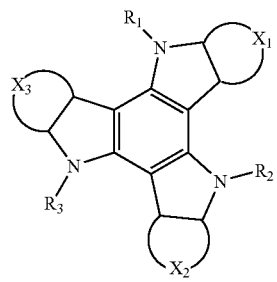

In Formula 1, R1 to R3 and X1 to X3 are as described in the specification. The compound of Formula 1 acts as a hole injection material, a hole transport material, a light emitting host, or a light emitting dopant in the organic light emitting device depending on the type of substituent.

8 Claims, 2 Drawing Sheets

[Figure 1]
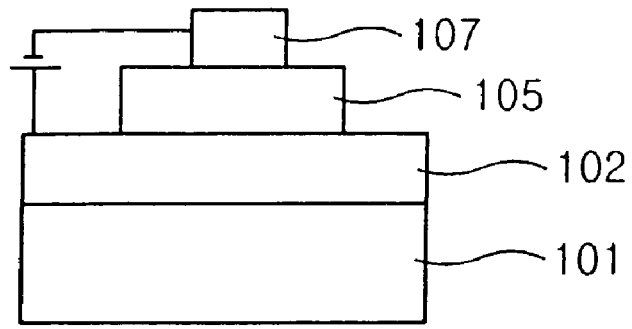
[Figure 2]
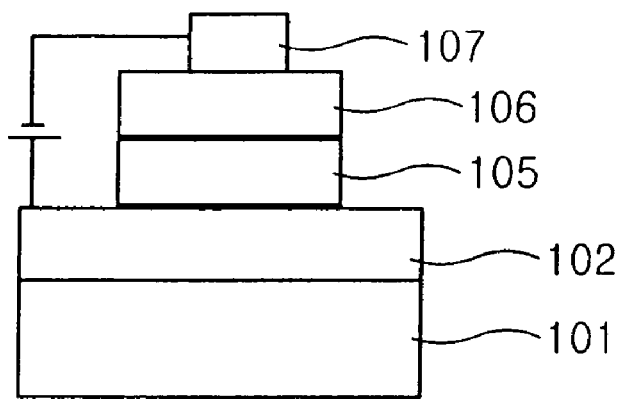
[Figure 3]
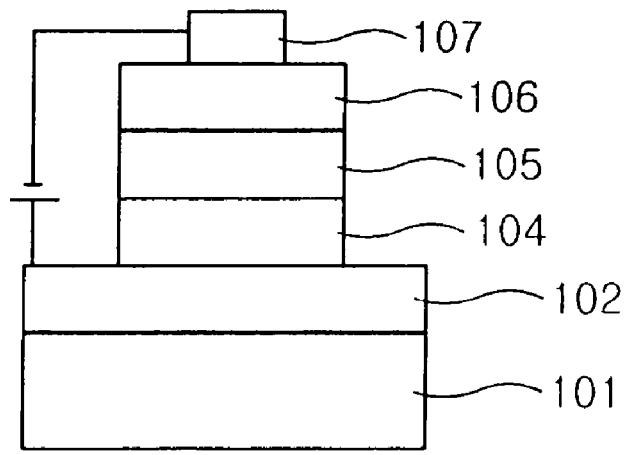

[Figure 4]
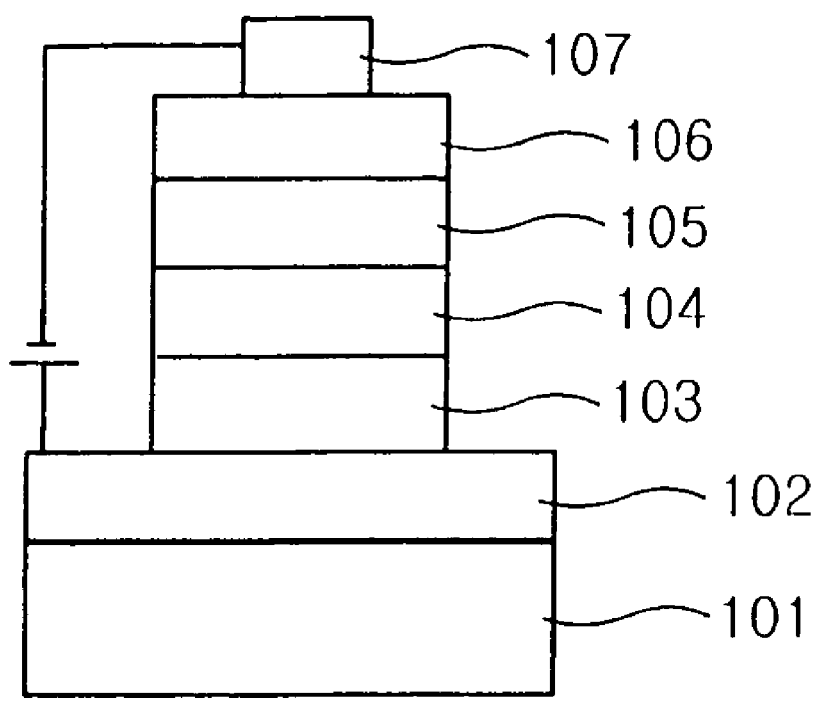

CARBAZOLE DERIVATIVE AND ORGANIC LIGHT EMITTING DEVICE USING SAME

This application claims the benefit of the filing date of Korean Patent Application Nos. 10-2004-0074920, filed on Sep. 20. 2004, in the Korean Intellectual Property Office, the disclosure of which is incorporated herein in its entirety by reference.

TECHNICAL FIELD

The present invention relates to a novel organic compound and an organic light emitting device using the same.

BACKGROUND ART

An organic light emitting device has a structure in which an anode, a cathode, and an organic material layer including a single molecule or polymers between these electrodes are layered, and is based on a mechanism in which an electron and a hole which are injected from the cathode and the anode into the organic material layer form an exciton, and in which light having certain wavelengths is generated when the exciton drops to a ground state.

The principle of the organic light emitting device was discovered for the first time by Pope et al. using a single crystal of anthracene in the year 1965. Subsequently, in the year 1987, Tang in Kodak Co. suggested an organic light emitting device having a function-separation type of laminate structure in which an organic material layer is divided into two layers: a hole transport layer and a light emitting layer. It was confirmed that high emission intensity of 1000 cd/m$^2$ or more was obtained at a low voltage not more than 10 V in the organic light emitting device (Tang, C. W.; VanSlyke, S. A. *Appl. Phys. Lett.* 1987, 51, 913). With this as an impetus, the organic electroluminescent device has started to be watched with keen interest, and, recently, many studies are being intensely conducted on an organic electroluminescent device having a function-separation type of laminate structure.

However, the organic light emitting device is problematic in that a light emitting lifetime is short, and durability and reliability are low. This is known to result from physical and chemical transformation, photochemical and electrochemical transformation, delamination, fusion, crystallization, and thermal decomposition of organic materials constituting layers of the organic light emitting device, and oxidation of a cathode. Accordingly, there is a need to develop an organic material which is capable of being used in the organic light emitting device and to avoid the above problems. Meanwhile, an organic material including carbazole, particularly an organic material having a linear structure which includes two carbazole molecules, has frequently been used for a long time as a drum photosensitive material for a duplicator or as a photoconductive material. Furthermore, a trimer type of tri-indole compound, which has a nonlinear structure as shown in the following Formula and includes three carbazoles, is known.

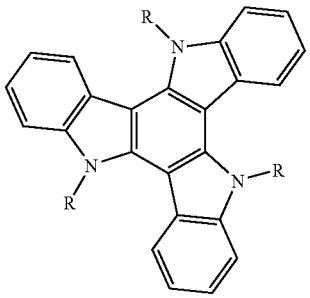

For example, a compound, in which R is H, CH3, or CH$_2$CH$_2$N(CH$_2$CH$_2$)$_2$O in the above Formula, was known long ago as a byproduct generated in a biochemistry field (J Org Chem 1998, 63(20), 7002-7008, Tetrahedron 1980, 36,1439). Japanese Patent Laid-Open Publication No. 2004-123619 discloses a compound, in which R in the above Formula is H as an effective component of a stabilizing agent for organic materials. Additionally, Japanese Patent Laid-Open Publication No. 2004-055240 discloses a compound having the basic structure of the above Formula as an electrode active material.

In an organic light emitting device field, many studies have been made into the use of a compound containing carbazole as a donor compound or a light emitting material capable of injecting or transporting holes. For example, Japanese Patent Laid-Open Publication No. 2001-261680 discloses the use of a compound in which R is an alkyl group having a carbon number of 2 to 24 in the above Formula as a photoconductive material, a nonlinear optical material, or an electroluminescent (EL) material.

However, in the case of the compound having the nonlinear trimer structure as described above, only a compound in which an amine group is substituted with hydrogen or an alkyl group can be generated or synthesized as a byproduct in the biochemistry field. Even if the compound having the trimer structure can be synthesized, synthesis thereof is difficult and the yield is very low, thus few studies have been made with respect to this. For example, when using the method disclosed in Japanese Patent Laid-Open Publication No. 2001-261680, only an alkyl group can be introduced to R in the above-mentioned Formula.

DISCLOSURE

[Technical Problem]

The present inventors have conducted extensive studies into the synthesis of a novel organic compound, resulting in the finding that the compound is used as a hole injection material, a hole transport material, a light emitting host, or a light emitting dopant in an organic light emitting device, thereby improving light emitting efficiency and stability of the device.

Accordingly, an object of the present invention is to provide a novel organic compound and an organic light emitting device using the same.

[Technical Solution]

The present invention provides a compound of the following Formula 1:

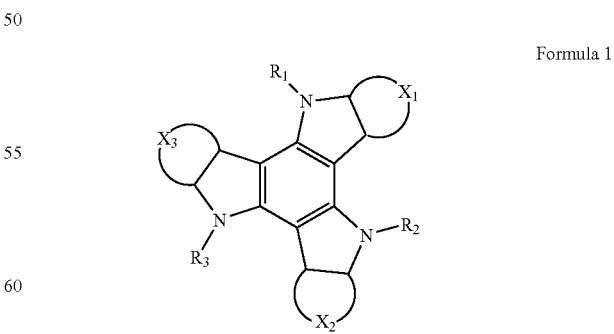

Formula 1

Wherein, X1 to X3 each are a substituted or unsubstituted benzene ring, or a substituted or unsubstituted 5-membered heterocyclic aromatic group which includes a ring source selected from the group consisting of O, S, and NR' (R' is selected from the group consisting of hydrogen, a substituted or unsubstituted alkyl group, and a substituted or unsubstituted aromatic group);

R1 to R3 each are a substituted or unsubstituted aromatic group or a substituted or unsubstituted heteroaromatic group with the proviso that X1 to X3 are substituted or unsubstituted benzene rings, and R1 to R3 are selected from the group consisting of hydrogen, a substituted or unsubstituted alkyl group, a substituted or unsubstituted aromatic group, and a substituted or unsubstituted heteroaromatic group with the proviso that X1 to X3 are substituted or unsubstituted 5-membered heterocyclic aromatic group.

Furthermore, the present invention provides an organic light emitting device which comprises a first electrode, one or more organic material layers, and a second electrode sequentially layered therein. One or more of the organic material layers include the compound of Formula 1.

DESCRIPTION OF DRAWINGS

FIG. 1 illustrates an organic light emitting device useful in the present invention;

FIG. 2 illustrates another organic light emitting device useful in the present invention;

FIG. 3 illustrates still another organic light emitting device useful in the present invention; and FIG. 4 illustrates yet another organic light emitting device useful in the present invention.

BEST MODE

Hereinafter, a detailed description will be given of the present invention. In an organic light emitting device field, it is known that carbazole or its derivatives can be used as a donor compound or a light emitting material capable of injecting or transporting holes. For example, the use of carbazole having an arylamine group introduced thereto as a hole transport material and a light emitting material is known (U.S. Pat. No. 6,649,722). However, as described in the Background Art, up to now, among compounds of carbazole and its derivatives, an organic material which is capable of assuring light emitting efficiency and stability of the organic light emitting device so as to commercialize the organic light emitting device has not been developed.

A study has been made into the use of trimer compounds of carbazole or its derivatives as a donor material or a light emitting material, which is capable of injecting or transporting holes, of an organic light emitting device. However, since it is difficult to synthesize the trimer compounds of carbazole or its derivatives, variety of the type of compounds has not been assured, thus there is a limit to the study of the usage of the above compounds.

The present inventors have conducted repeated studies into trimer compounds of carbazole or its derivatives, resulting in the synthesis of a novel compound of the following Formula 1.

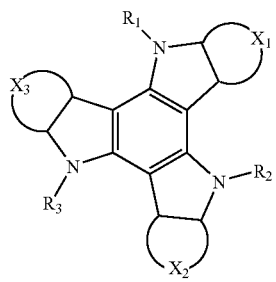

Formula 1

In the above Formula 1, X1 to X3 and R1 to R3 are the same as in the above-mentioned definition.

Representative examples of the compound of Formula 1 include a compound of Formula 2 and a compound of Formula 3.

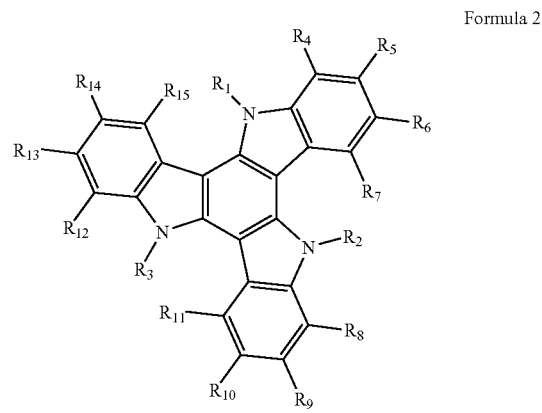

Formula 2

In the above Formula 2, R1 to R3 are a substituted or unsubstituted aromatic group, or a substituted or unsubstituted heteroaromatic group, and R4 to R15 are each selected from the group consisting of hydrogen, a halogen atom, a nitrile group (CN), a nitro group ($NO_2$), a formyl group, an acetyl group, a benzoyl group, an amide group, a styryl group, an acetylene group, a quinoline group, a quinazoline group, a phenanthroline group, a cuproin group, a substituted or unsubstituted alkyl group, a substituted or unsubstituted aromatic group, a substituted or unsubstituted aralkyl group, a substituted or unsubstituted arylamine group, a substituted or unsubstituted alkylamine group, a substituted or unsubstituted aralkylamine group, and a substituted or unsubstituted heterocyclic group.

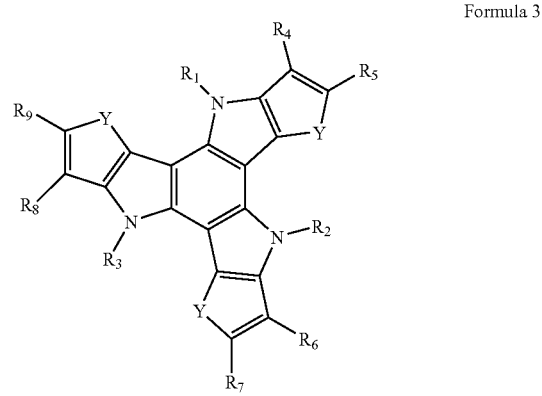

Formula 3

In the above Formula 3:

R1 to R3 each are selected from the group consisting of hydrogen, a substituted or unsubstituted alkyl group, a substituted or unsubstituted aromatic group, and a substituted or unsubstituted heteroaromatic group;

R4 to R9 each are selected from the group consisting of hydrogen, a halogen atom, a nitrile group (CN), a nitro group ($NO_2$), a formyl group, an acetyl group, a benzoyl group, an amide group, a styryl group, an acetylene group, a quinoline group, a quinazoline group, a phenanthroline group, a cuproin group, a substituted or unsubstituted alkyl group, a substituted or unsubstituted aromatic group, a substituted or unsubstituted aralkyl group, a substituted or unsubstituted arylamine group, a substituted or unsubstituted alkylamine group, a substituted or unsubstituted aralkylamine group, and a substituted or unsubstituted heterocyclic group; and Y is selected from the group consisting of O, S, and NR' (R' is selected from the group consisting of hydrogen, a substituted or unsubstituted alkyl group, and a substituted or unsubstituted aromatic group).

Structural characteristics of compounds of Formulae 2 and 3, and their effects are as follows.

The compound of the above Formula 2 has a trimer structure including three carbazoles, in which an amine group of carbazole is substituted with an aromatic group. The compound of the above Formula 3 has a trimer structure including three carbazole derivatives in which a 5-membered hetero ring such as thiophene is positioned at the position of one benzene of carbazole.

In the compounds of Formulae 2 and 3, monomers, that is, carbazole or its derivatives, constituting the trimer do not affect each other in view of chemical structures. Furthermore, in the above compounds, an increase in a conjugation length due to trimerization is not so big as in a compound having a linear structure. For the same reason, in the compounds of Formulae 2 and 3, optical, spectroscopic, and electrochemical properties of the monomers are not changed significantly.

Accordingly, the compounds of Formulae 2 and 3 have intrinsic properties of carbazole and carbazole derivatives in which the 5-membered hetero ring such as thiophene is positioned at one benzene of carbazole, that is, hole injection or transport properties and/or light emitting properties in the organic light emitting device. Thus, the compounds of Formulae 2 and 3 can act as a hole injection material, a hole transport material, a light emitting host, or a light emitting dopant in the organic light emitting device.

Additionally, since molecular weight increases while the intrinsic properties of carbazole or its derivatives are maintained in the compounds of Formulae 2 and 3, they are thermally more stable than compounds of the monomers. Therefore, the compounds of the present invention can increase the life of the organic light emitting device.

Furthermore, as described above, since the compounds of Formulae 2 and 3 have conjugation lengths that are relatively shorter than those of compounds having linear structures, an energy band gap is wide, thus they are used as a host material, along with fluorescent guest materials and particularly phosphorescent guest materials, in the organic light emitting device.

Meanwhile, in the compound of Formula 2, an amine group is substituted with an aromatic group with respect to the conventional carbazole trimer compound in which an amine group is substituted with hydrogen or an alkyl group. In Formula 2, the aromatic group substituting the amine group affects a HOMO (highest occupied molecular orbital) energy level of the compound, unlike hydrogen or the alkyl group. Accordingly, the HOMO energy level of the compound of Formula 2 as the hole injection and/or transport material or the light emitting material is optimized depending on the type of aromatic group substituting the amine group, and preferably, depending on the number of amine contained in the aromatic group.

Based on the above description, the compound of Formula 2 can improve the stability of holes, hole transport properties and/or light emitting properties of the organic light emitting device in comparison with the carbazole trimer compound, in which the amine group is substituted with hydrogen or the alkyl group as disclosed in the prior art.

Thereby, efficiency of the device is improved. For example, in the compound of the present invention, an aromatic group having excellent light emitting efficiency is introduced to the amine group, thereby a light emitting material having excellent light emitting properties, for example, a host material or a dopant material, is prepared.

Even though the compound of Formula 2 has the above-mentioned advantages, it has not been synthesized in the prior art due to difficulty in synthesis. Thus, there has been no study of the usage of the above compound. A method of producing the compound of Formula 2 will be described later.

The above-mentioned basic physical properties of the compound according to the present invention result from a structure in which carbazole is trimerized like the compound of Formula 2 and the amine group of carbazole is substituted with the aromatic group, or a structure in which the carbazole derivatives where the 5-membered hetero ring such as thiophene is positioned at one benzene of carbazole are trimerized like Formula 3. Since the basic structure of the compound of the present invention is not changed depending on the substituents of the compound, the basic physical properties of the compound according to the present invention are not changed depending on the substituents. However, in the compounds of Formulae 2 and 3, the degree of realization of basic physical properties, emission wavelength of light and/or other incidental properties are changed depending on the types of substituents.

The method of producing the compound according to the present invention is as follows. In the prior art, the compounds of Formula 2 and Formula 3 cannot be synthesized because it is difficult to synthesize trimer compounds of carbazole or its derivatives.

Particularly, the compound of Formula 2, in which the amine group is substituted with the aromatic group in the carbazole trimer, cannot be produced using the method of producing the conventional carbazole trimer compound, in which the amine group is substituted with the alkyl group in the carbazole trimer. For example, in the prior art, in order to produce the compound in which the amine group of the carbazole trimer is substituted with the alkyl group, a carbazole monomer, in which the amine group is substituted with the alkyl group, is produced and then trimerized. With the above conventional procedure, however, it is impossible to produce the compound of Formula 2, in which the amine group is substituted with the aromatic group.

After the compound of Formula 4 is produced, the compound of Formula 4, a precursor of the aromatic compound which will substitute the amine group, Na(t-BuO), a Pd$_2$(dab)$_3$ catalyst, and a 2-(di-t-butylphosphino)diphenyl ligand are reacted in a xylene solvent to produce the compound of Formula 2.

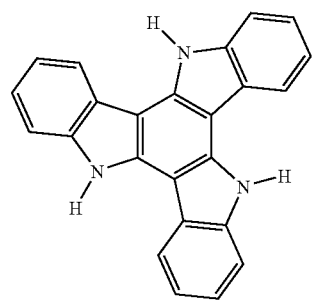

Formula 4

The compound of Formula 3 may be produced using a method in which a carbazole derivative monomer where a 5-membered hetero ring such as thiophene are positioned at one benzene of carbazole is trimerized and a substituent is introduced to an amine group of the carbazole derivative, or a method in which the amine group of the carbazole derivative monomer is substituted with the substituent and the monomer is then trimerized.

Examples of the halogen atom of the substituents of Formulae 2 and 3 include fluorine (F), chlorine (Cl), bromine (Br), and iodine (I).

An alkyl group of the substituents of Formulae 2 and 3 preferably has a carbon number of 1-20, and is exemplified by a straight chain alkyl group, such as a methyl group, an ethyl group, a propyl group, or a hexyl group, and a branched chain alkyl group, such as an isopropyl group or a t-butyl group.

Examples of an aromatic group of the substituents of Formulae 2 and 3 include a monocyclic aromatic group, such as a phenyl group, a polycyclic aromatic group, such as naphthyl, anthryl, pyrene, and perylene, and a heterocyclic aromatic group, such as pyridine.

Examples of an aralkyl group of the substituents of Formulae 2 and 3 include an alkyl group having a carbon number of 1-20 which is substituted with aromatic hydrocarbons, such as phenyl, biphenyl, naphthyl, terphenyl, anthryl, pyrel, and perylene.

Examples of an arylamine group of the substituents of Formulae 2 and 3 include an amine group which is substituted with aromatic hydrocarbons, such as phenyl, biphenyl, naphthyl, terphenyl, anthryl, pyrene, and perylene.

Examples of an alkylamine group of the substituents of Formulae 2 and 3 include an amine group which is substituted with aliphatic hydrocarbons having a carbon number of 1-20.

Examples of an aralkylamine group of the substituents of Formulae 2 and 3 include an amine group which is substituted with aromatic hydrocarbons, such as phenyl, biphenyl, naphthyl, terphenyl, anthryl, pyrene, and perylene, and aliphatic hydrocarbons having a carbon number of 1 - 20.

Examples of a heterocyclic group of the substituents of Formulae 2 and 3 include a pyrrolyl group, a thienyl group, an indole group, an oxazol group, an imidazole group, a thiazol group, a pyridyl group, a pyrimidine group, a piperazine group, a thiophene group, a furan group, and a pyridazinyl group.

Substituted alkyl, aromatic, aralkyl, arylamine, alkylamine, aralkylamine, and heterocyclic groups of the substituents of Formulae 2 and 3 may include a halogen atom, such as fluorine, chlorine, bromine, and iodine, a nitrile group, a nitro group, a formyl group, an acetyl group, an arylamine group, an alkylamine group, an aralkylamine group, a benzoyl group, an amide group, a styryl group, an acetylene group, a phenyl group, a naphthyl group, an anthryl group, a pyrene group, a perylene group, a pyridyl group, a pyridazyl group, a pyrrolyl group, an imidazolyl group, a quinolyl group, an anthrone group, an acridone group, and an acridine group.

In an embodiment of the present invention, the compound of Formula 2 may be a compound in which R1 to R3 each are substituted or unsubstituted aromatic groups; R6, R10, and R14 each are selected from the group consisting of a halogen atom, a nitrile group (CN), a nitro group ($NO_2$), a formyl group, an acetyl group, a benzoyl group, an amide group, a styryl group, an acetylene group, a quinoline group, a quinazoline group, a phenanthroline group, a cuproin group, a substituted or unsubstituted alkyl group, a substituted or unsubstituted aromatic group, a substituted or unsubstituted aralkyl group, a substituted or unsubstituted arylamine group, a substituted or unsubstituted alkylamine group, a substituted or unsubstituted aralkylamine group, and a substituted or unsubstituted heterocyclic group; and R4, R5, R7, R8, R9, R11, R12, R13, and R15 are hydrogen in Formula 2.

In an embodiment of the present invention, the compound of Formula 3 may be a compound in which R1 to R3 each are selected from the group consisting of hydrogen, a substituted or unsubstituted alkyl group, and a substituted or unsubstituted aromatic group; R5, R7, and R9 each are selected from the group consisting of a halogen atom, a nitrile group (CN), a nitro group ($NO_2$), a formyl group, an acetyl group, a benzoyl group, an amide group, a styryl group, an acetylene group, a quinoline group, a quinazoline group, a phenanthroline group, a cuproin group, a substituted or unsubstituted alkyl group, a substituted or unsubstituted aromatic group, a substituted or unsubstituted aralkyl group, a substituted or unsubstituted arylamine group, a substituted or unsubstituted alkylamine group, a substituted or unsubstituted aralkylamine group, and a substituted or unsubstituted heterocyclic group; and R4, R6, and R8 are hydrogen in Formula 3.

Illustrative, but non-limiting examples of the compound of Formula 2 include Formulae 2-1 to 2-23.

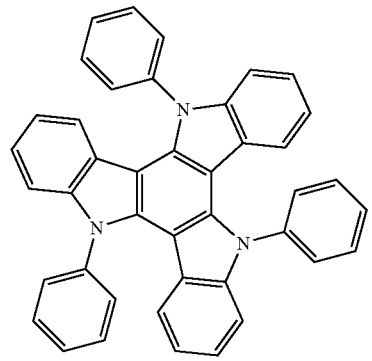

Formula 2-1

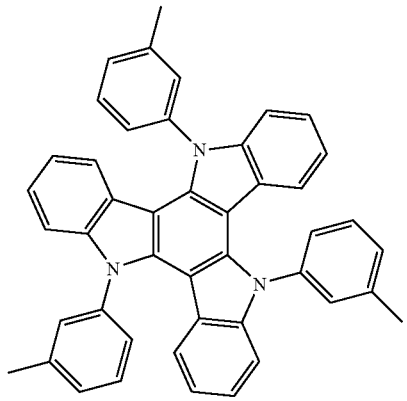

Formula 2-2

-continued
Formula 2-3
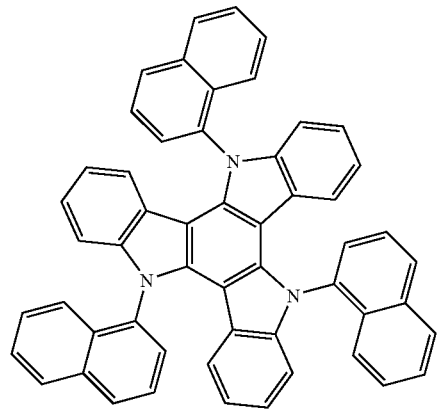
Formula 2-4
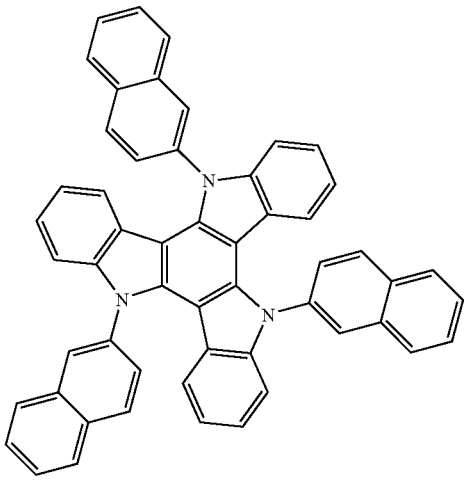
Formula 2-5
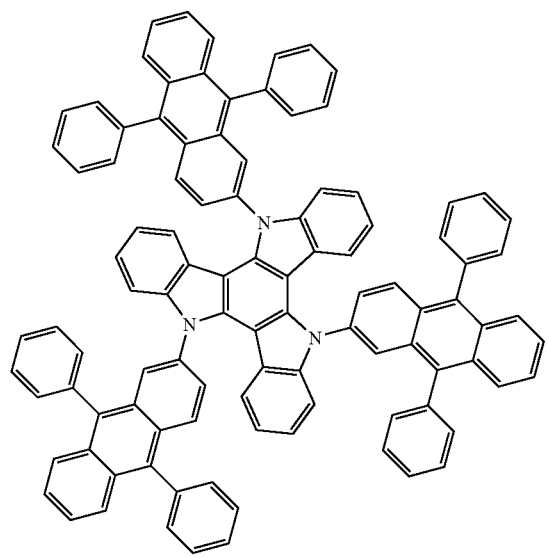
Formula 2-6
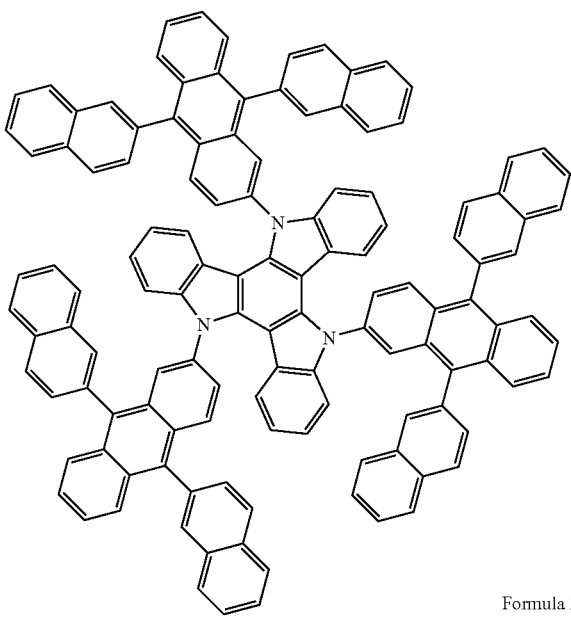
Formula 2-7
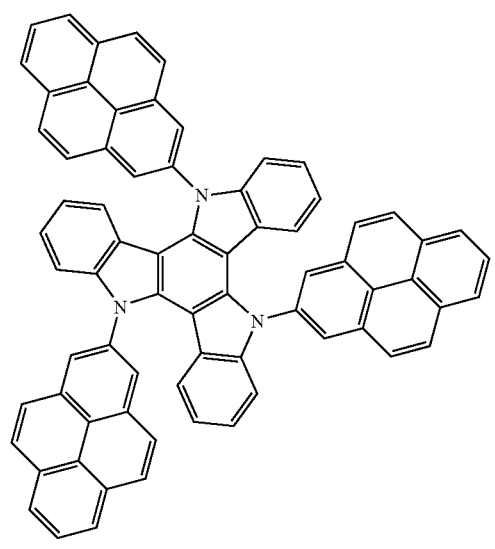
Formula 2-8
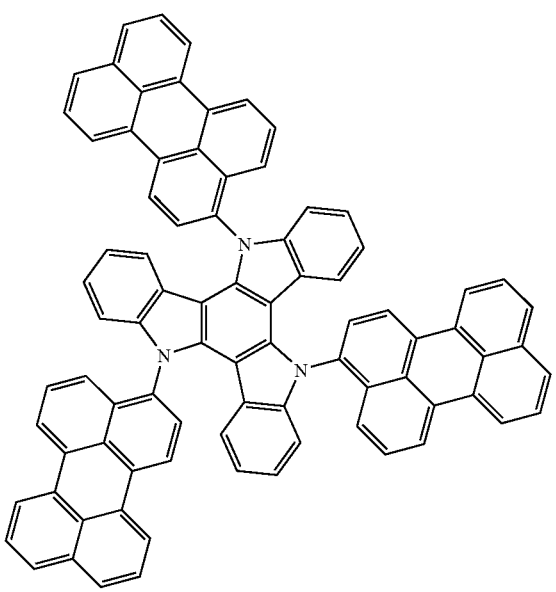

-continued
Formula 2-9
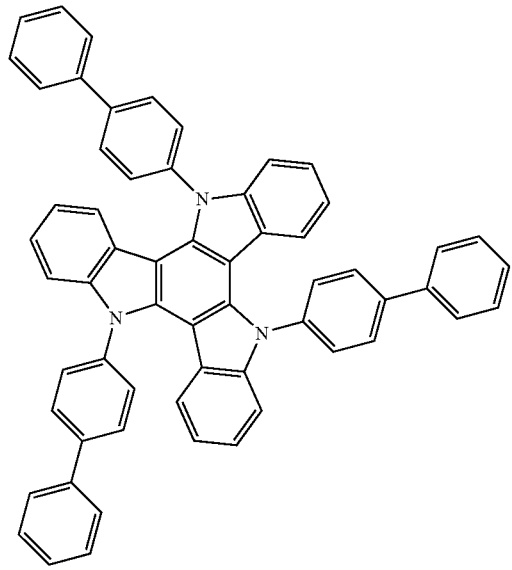
Formula 2-10
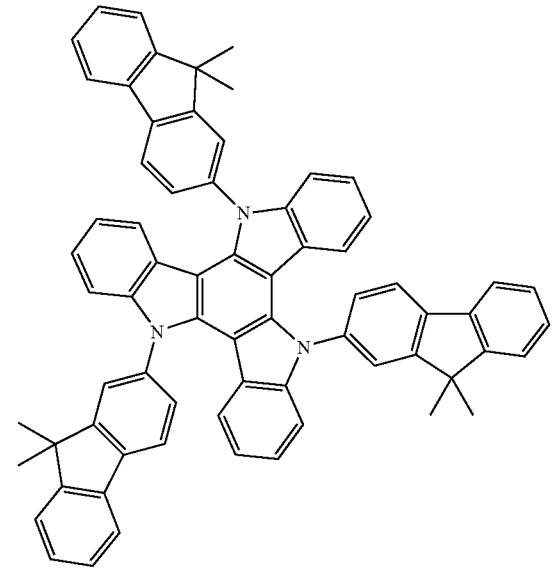
Formula 2-11
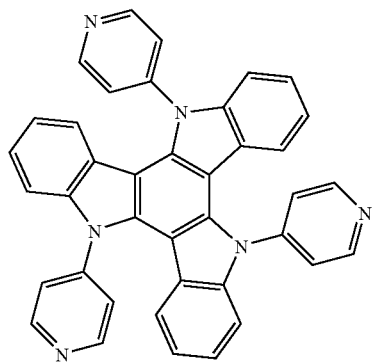
Formula 2-12
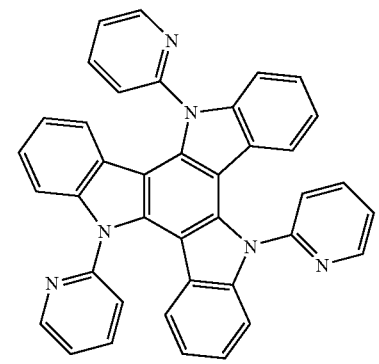
Formula 2-13
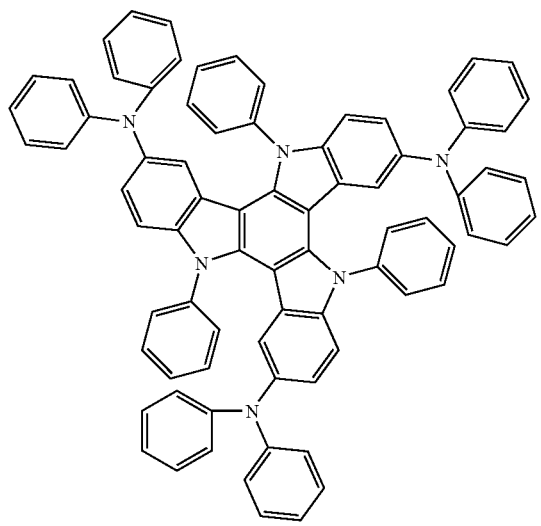
Formula 2-14
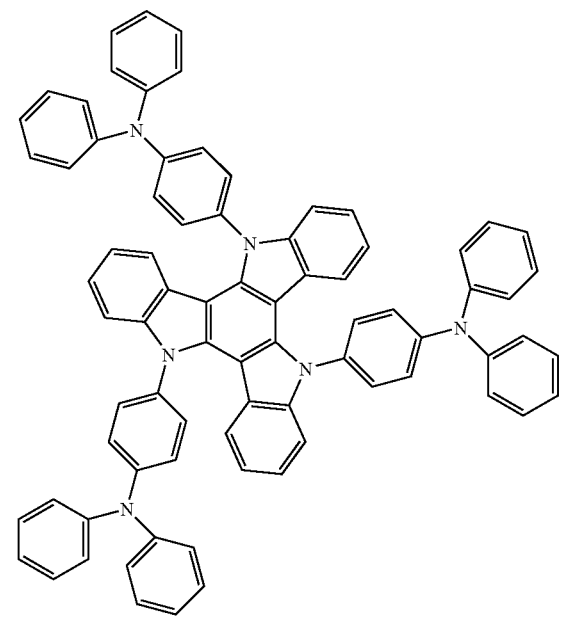

Formula 2-15
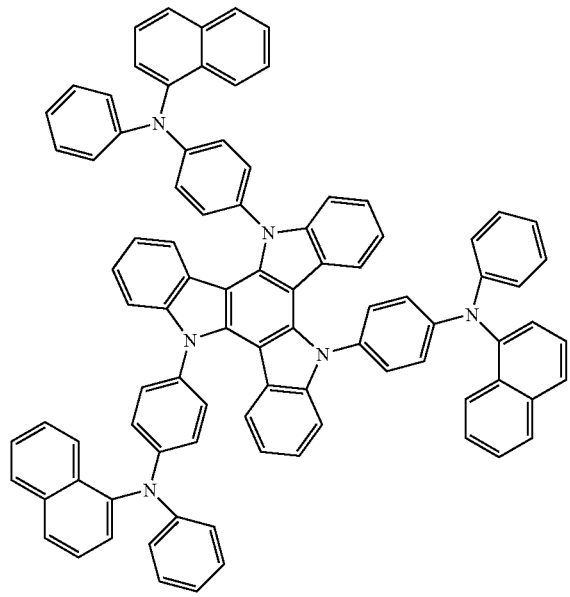
Formula 2-16
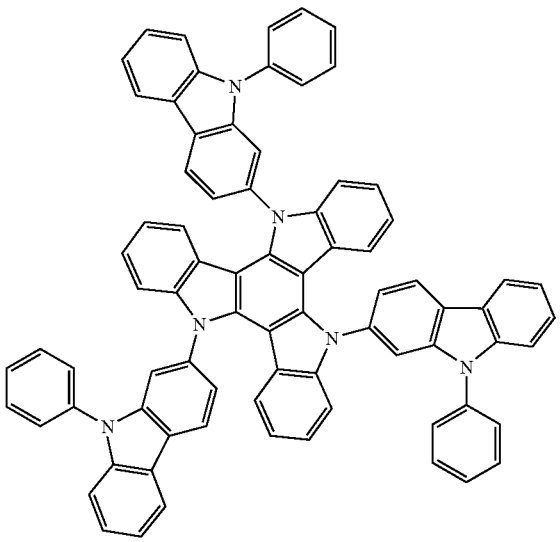
Formula 2-17
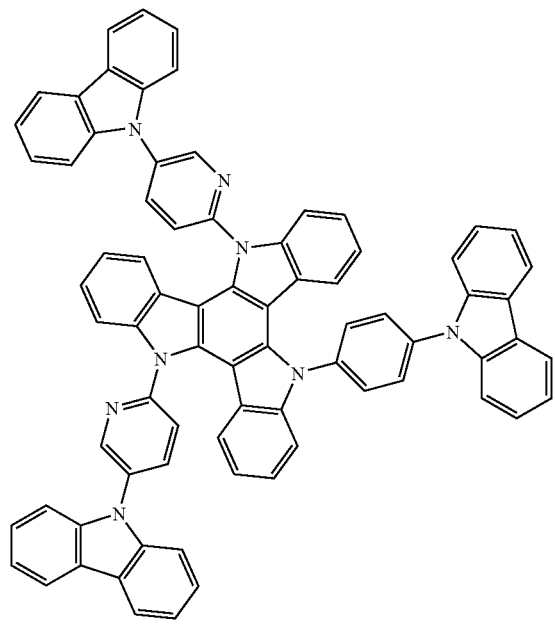
Formula 2-18
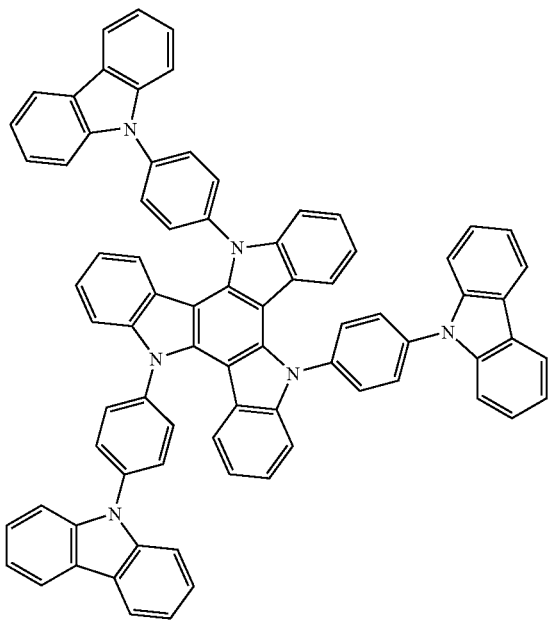

-continued
Formula 2-19
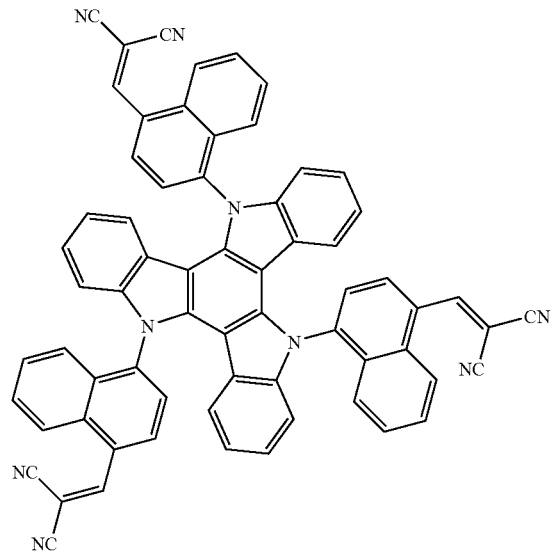
Formula 2-20
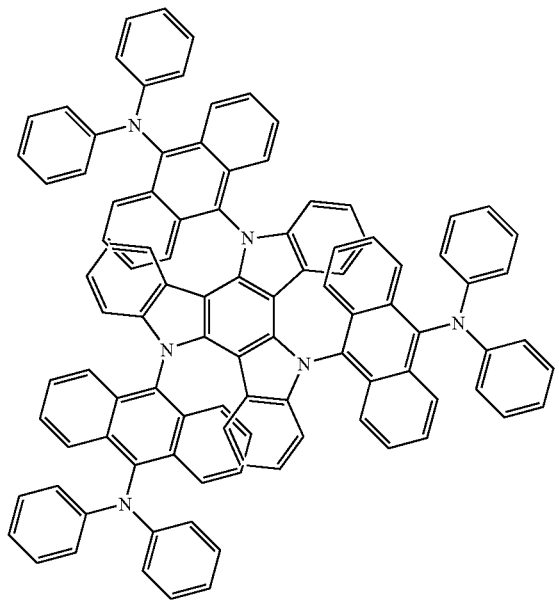
Formula 2-21
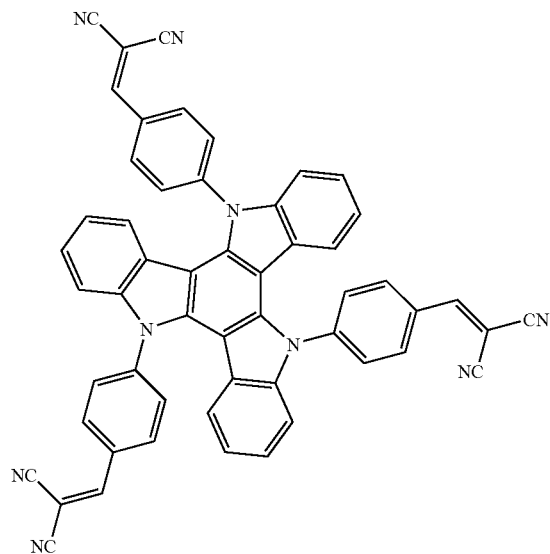

Formula 2-22
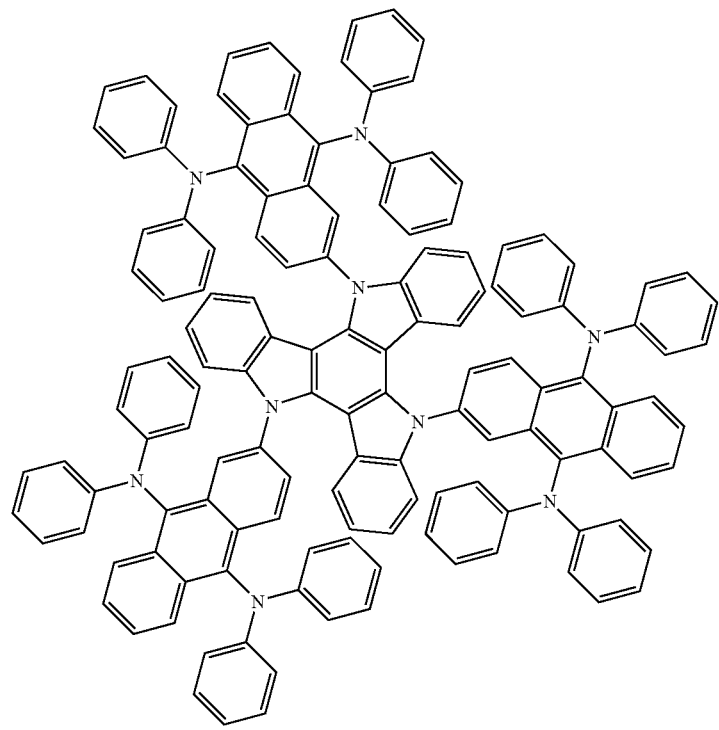
Formula 2-23
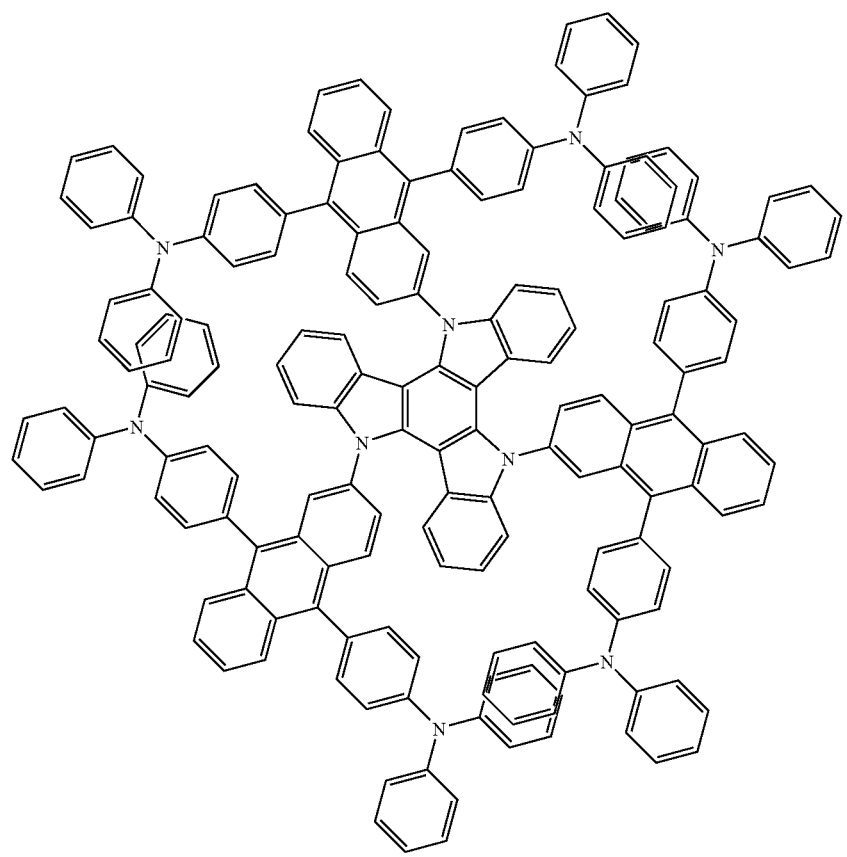

Illustrative, but non-limiting examples of the compound of Formula 3 include Formulae 3-1 to 3-4.
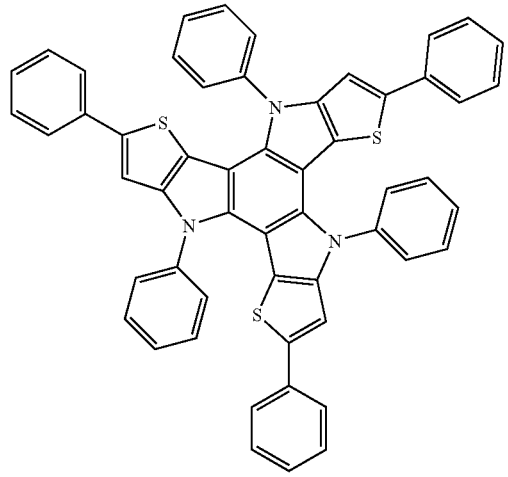
Formula 3-1
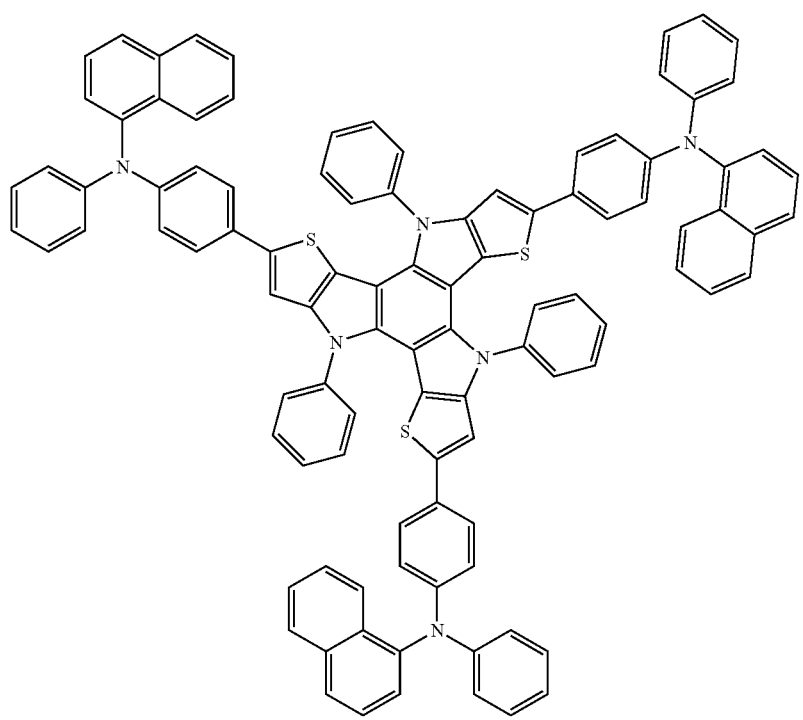
Formula 3-2

-continued

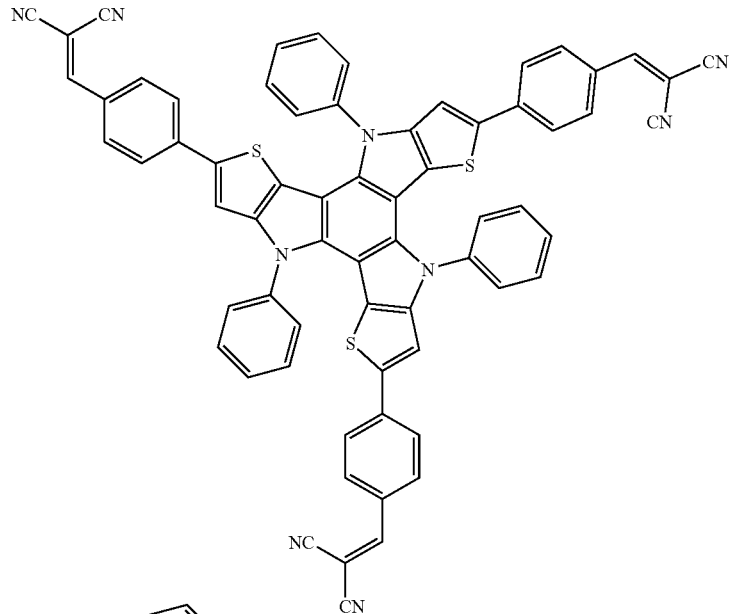

Formula 3-3

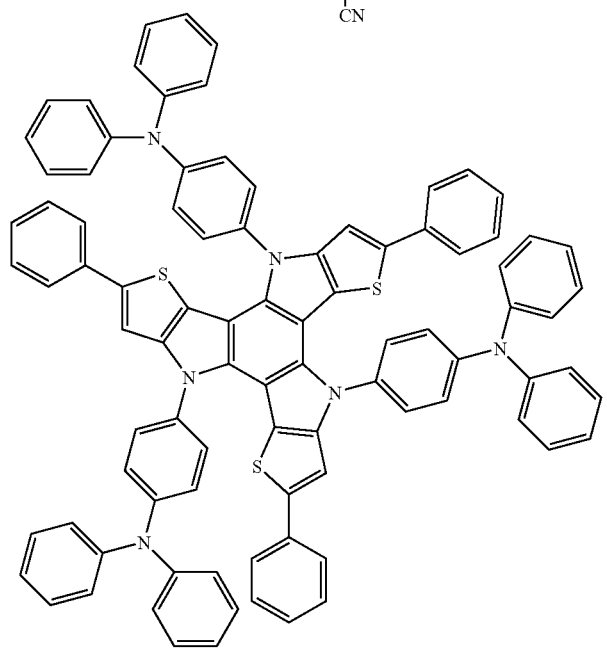

Formula 3-4

Furthermore, the present invention provides an organic light emitting device which comprises a first electrode, one or more organic material layers, and a second electrode sequentially layered therein. One or more layers of the organic material layers comprise the compound of the above Formula 1.

The organic material layer of the organic light emitting device according to the present invention may have a single layer structure, or alternatively, a multilayered structure in which two or more organic material layers are layered. For example, as the organic material layer, the organic light emitting device of the present invention may have a hole injection layer, a hole transport layer, a light emitting layer, an electron transport layer, an electron injection layer, or a buffer layer interposed between the anode and the hole injection layer. However, the structure of the organic light emitting device is not limited to this, but may comprise a smaller number of organic material layers.

Illustrative, but non-limiting examples of the structures of the organic light emitting device according to the present invention are shown in FIGS. 1 to 4.

FIG. 1 illustrates the structure of an organic light emitting device in which an anode 102, a light emitting layer 105, and a cathode 107 are sequentially layered on a substrate 101 in this structure, the light emitting layer 105 may be formed using the compound of Formula 1.

FIG. 2 illustrates the structure of an organic light emitting device in which an anode 102, a hole transport and light emitting layer 105, a light emitting and electron transport layer 106, and a cathode 107 are sequentially layered on a substrate 101 in this structure, the hole transport and light emitting layer 105 may be formed using the compound of Formula 1.

FIG. 3 illustrates the structure of an organic light emitting device in which a substrate 101, an anode 102, a hole injection and transport layer 104, a light emitting layer 105, an electron transport layer 106, and a cathode 107 are sequentially layered in this structure, the hole injection and transport layer 104 and/or the light emitting layer 105 may be formed using the compound of Formula 1.

FIG. 4 illustrates the structure of an organic light emitting device in which a substrate 101, an anode 102, a hole injection layer 103, a hole transport layer 104, a light emitting layer 105, an electron transport layer 106, and a cathode 107 are sequentially layered in this structure, the hole injection layer 103, the hole transport layer 104, and/or the light emitting layer 105 may be formed using the compound of Formula 1.

In the organic light emitting device of the present invention, the layer including the compound of Formula 1 may be formed between the anode and the cathode through a vacuum deposition method or a solution coating method. Illustrative, but non-limiting examples of the solution coating method include a spin coating method, a dip coating method, a doctor blading method, an inkjet printing method, and a heat transcription method.

The thickness of the organic material layer containing the compound of Formula 1 is 10 μm or less, preferably 0.5 μm or less, and more preferably 0.001-0.5 μm.

The layer including the compound of Formula 1 may further comprise other materials which are capable of conducting injection of holes, transport of the holes, light emission, transport of electrons, and injection of the electrons known in the art, if necessary.

The organic light emitting device of the present invention can be produced using known materials through a known process, modified only in that one or more layers of organic material layers include the compound of the present invention, that is, the compound of Formula 1.

For example, the organic light emitting device of the present invention may be produced by sequentially layering a first electrode, an organic material layer, and a second electrode on a substrate. In connection with this, a physical vapor deposition (PVD) method, such as a sputtering method or an e-beam evaporation method, may be used, but the method is not limited to these.

[Mode for Invention]

A better understanding of the present invention may be obtained in light of the following examples which are set forth to illustrate, but are not to be construed to limit the present invention.

Preparation of a compound of Formula 4

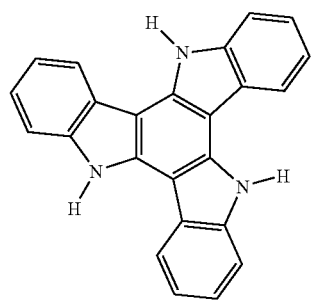

Formula 4

A mixture of oxindole (1.3 g, 10 mmol) and 5 mL of POCl$_3$ was reacted at 120° C. for 15 hours.

After the reaction was completed, excess POCl$_3$ was removed by distillation, 10 mL of ice water were added to the remaining product, and sat. Na$_2$CO$_3$ was added thereto to conduct neutralization. Subsequently, the reactants were filtered, washed with water and ethanol, and vacuum dried. The resulting compound was separated using column chromatography (ethyl acetate: n-Hexane=1:4) to produce the pure compound of Formula 4 (0.65 g, Yield=54%): MS[M+1]$^+$ 346.

PREPARATION EXAMPLE 1

Preparation of a compound of Formula 2-1

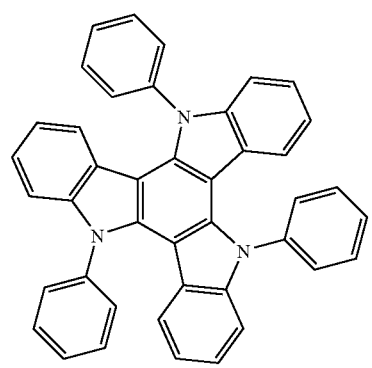

Formula 2-1

0.13 g (1.36 mmol) of Na(t-BuO), 331 mg (0.03 mmol) of Pd$_2$(dba)$_3$, and 10 mg (0.05 mmol) of 2-(di-t-butylphosphino)diphenyl were added to a mixture of 1.2 g (3.4 mmol) of the compound of Formula 4 and 2.8 g (1.36 mmol) of iodobenzene in 70 mL of xylene, and reacted at 120° C. for 1 hour. After the reaction was finished, cooling to room temperature was conducted, and the precipitate was filtered, washed with water and ethanol, and vacuum dried. The resulting compound was dissolved in 80 mL of a THF solvent, and treated with acidic white clay to remove inorganic metals, such as Pd. The filtrate was concentrated and precipitated in ethanol. The precipitate was then vacuum dried (1.0 g, Yield=62%): Mp 357° C. (DSC); MS[M+1]$^+$ 574.

PREPARATION EXAMPLE 2

Preparation of the compound of Formula 2-2

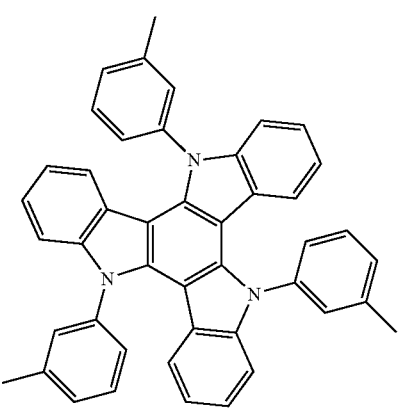

Formula 2-2

The procedure of preparation example 1 was repeated to produce the compound of Formula 2-2 except that 3-iodotoluene was used instead of iodobenzene. (1.2 g, Yield=58%): Mp≧380° C., T$_g$ 149.8° C. (DSC); MS[M+1]$^+$ 616

PREPARATION EXAMPLE 3

Preparation of the compound of Formula 2-9

Formula 2-9

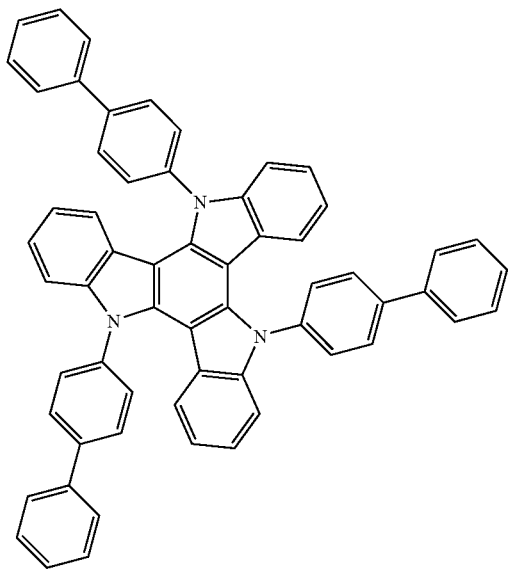

The procedure of preparation example 1 was repeated to produce the compound of Formula 2-9 except that 4-bromo-biphenyl was used instead of iodobenzene. (1.5 g, Yield=56%):Mp 374.4° C. (DSC); MS[M+1]$^+$ 802

PREPARATION EXAMPLE 4

Preparation of the compound of Formula 2-15

Formula 2-15

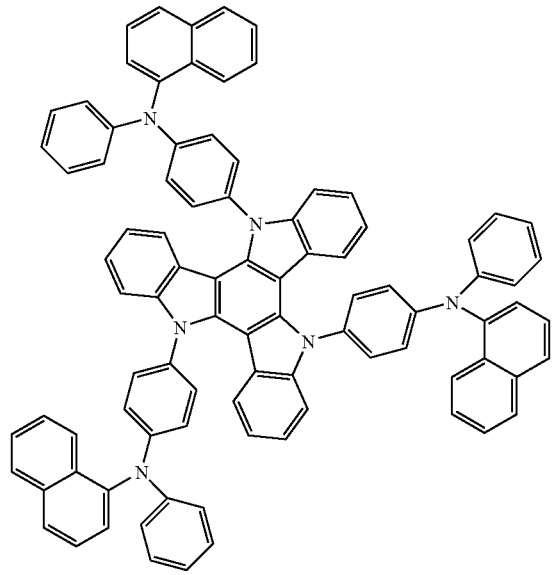

The procedure of preparation example 1 was repeated to produce the compound of Formula 2-15 except that N-(4-bromophenyl)-N-naphthyl-1-yl-N-phenylamine was used instead of iodobenzene.

(1.9 g, Yield=45%):Mp 360.9° C. T$_g$ 189.7° C. (DSC); MS[M+1]$^+$ 1225

PREPARATION EXAMPLE 5

Preparation of the compound of Formula 3-1

Formula 3-1

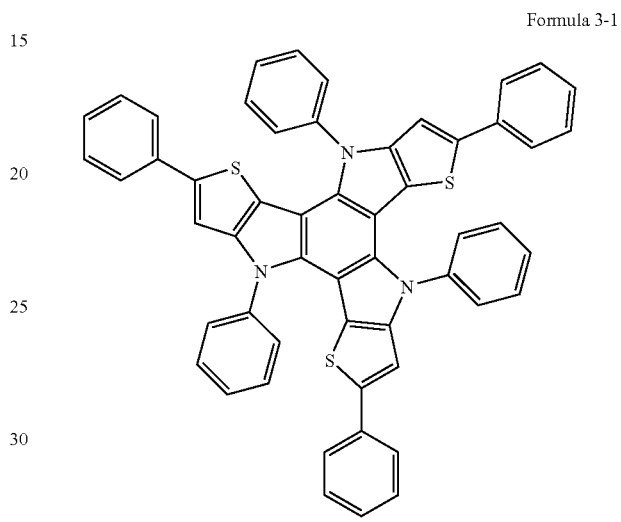

Scheme for Synthesis of Formula 3-1

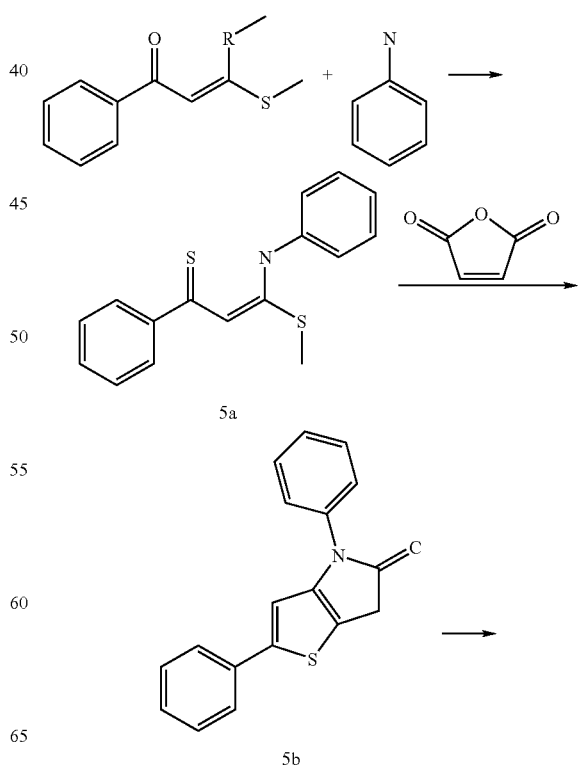

-continued

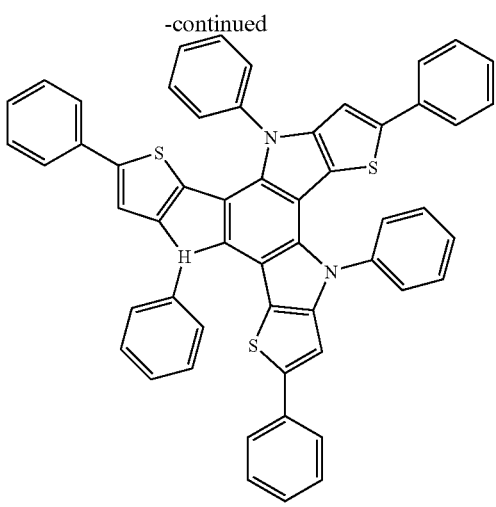

Preparation of the compound of Formula 5a

The same procedure disclosed in *Chem. Pharm. Bull.* 1993, 41, 1293-1296 was used to prepare the compound of Formula 5a.

MS [M+1]$^+$ 286.

Preparation of the compound of Formula 5b

The same procedure disclosed in *J. Org. Chem.* Vol. 69, No. 14, 2004 was used to prepare the compound of Formula 5b.

MS [M+1]+292.

Preparation of the compound of Formula 3-1

A mixture of compound 5b (2.9 g, 10 mmol) and 5 mL of POCl$_3$ was reacted at 100° C. for 10 hours.

After the reaction was completed, excess POCl$_3$ was removed by distillation, 10 mL of ice water were added to the remaining product, and saturated Na$_2$CO$_3$ was added thereto to conduct neutralization. Subsequently, the reactants were filtered, washed with water and ethanol, and dried under vacuum. The resulting compound was separated using column chromatography (ethyl acetate:n-Hexane=1:10) to produce the pure compound of Formula 3-1 (1.6 g, Yield=60%): MS [M+1]+820.

EXAMPLE 1

Preparation of an Organic Light Emitting Device

A glass substrate, on which ITO (indium tin oxide) was applied to a thickness of 1500 Å to form a thin film, was put in distilled water, in which a detergent was dissolved, and washed for 30 min using ultrasonic waves. Subsequently, ultrasonic washing was conducted in distilled water twice for 10 min. A product manufactured by Fischer Inc. was used as the detergent, and distilled water was produced by filtering twice using a filter manufactured by Millipore Inc. After the washing using distilled water was finished, ultrasonic washing was conducted sequentially using isopropyl alcohol, acetone, and methanol solvents, and drying was then conducted. Next, it was transported to a plasma washing machine. Subsequently, the substrate was washed using nitrogen plasma for 5 min, and then transported to a vacuum evaporator. Hexanitrile hexaazatriphenylene of the following Formula 5 was vacuum deposited to a thickness of 500 Å by heating on a transparent ITO electrode, which was prepared through the above procedure, so as to form a hole injection layer. The compound of Formula 2-1, which was a material transporting holes and was produced in preparation example 1, was vacuum deposited thereonto in a thickness of 400 Å, and the compound (Alq3) of Formula 6 was vacuum deposited thereonto in a thickness of 300 Å, to form a light emitting layer. A compound of Formula 7 was vacuum deposited on the light emitting layer to a thickness of 200 Å so as to form an electron transport layer. Lithium fluoride (LiF) having a thickness of 10 Å and aluminum having a thickness of 2500 Å were sequentially deposited to form a cathode.

In the above procedure, the deposition speed of an organic material was maintained at 1 Å/sec, and lithium fluoride and aluminum were deposited at a speed of 0.2 Å/sec and 3-7 Å/sec, respectively.

In the resulting organic light emitting device, an intrinsic green spectrum of Alq3 having brightness of 4000 cd/m$^2$ was observed at a forward current density of 100 mA/cm$^2$, and corresponded to x of 0.34 and y of 0.56 based on a 1931 CIE color coordinate.

Formula 5

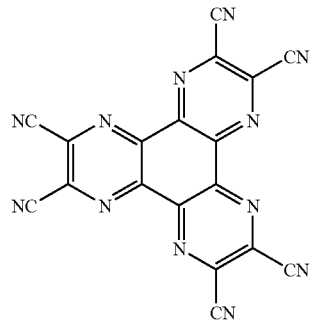

Formula 6

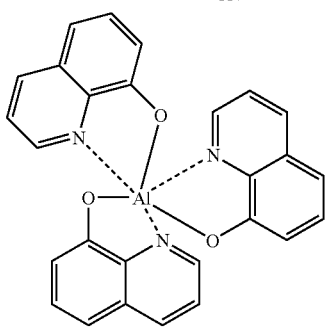

Formula 7

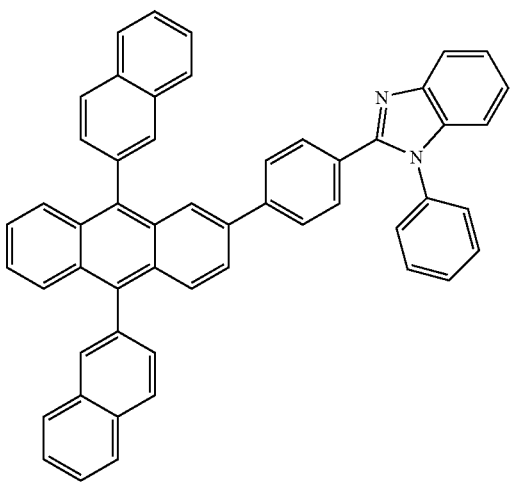

EXAMPLE 2

The procedure of example 1 was repeated to produce an organic light emitting device except that the compound of Formula 2-2 was used as a hole transport material instead of the compound of Formula 2-1.

In the resulting organic light emitting device, an intrinsic green spectrum of Alq3 having brightness of 4960 cd/m² was observed at a forward current density of 100 mA/cm², and corresponded to x of 0.33 and y of 0.56 based on a 1931 CIE color coordinate.

EXAMPLE 3

The procedure of example 1 was repeated to produce an organic light emitting device, except that the compound of Formula 2-9 was used as a hole transport material instead of the compound of Formula 2-1.

In the resulting organic light emitting device, an intrinsic green spectrum of Alq3 having brightness of 4959 cd/m² was observed at a forward current density of 100 m cm², and corresponded to x of 0.33 and y of 0.56 based on a 1931 CIE color coordinate.

COMPARATIVE EXAMPLE 1

The procedure of example 1 was repeated to produce an organic light emitting device except that NPB, which was conventionally known as a hole transport material, was vacuum deposited to a thickness of 400 Å on a hole injection layer instead of the compound of Formula 2-1 to form a hole transport layer.

In the resulting organic light emitting device, an intrinsic green spectrum of Alq3 having brightness of 340 cd/m² was observed at a forward current density of 100 mA/cm², and corresponded to x of 0.32 and y of 0.56 based on a 1931 CIE color coordinate.

From the results of the above-mentioned examples and comparative example, it can be seen that the compounds of the present invention function to transport holes like NPB, which is a conventional hole transport material, and improve the efficiency of a device at the same current density in comparison with NPB.

INDUSTRIAL APPLICABILITY

A compound of the present invention is a novel compound which acts as a hole injection material, a hole transport material, a light emitting host, or a light emitting dopant in an organic light emitting device.

The invention claimed is:

1. A compound of Formula 1:

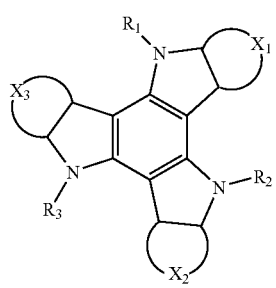

Formula 1 wherein, $X_1$ to $X_3$ each are a substituted or unsubstituted benzene ring, or a substituted or unsubstituted 5-membered heterocylic aromatic group which includes a ring member selected from the group consisting of O, S, and NR' (R' is selected from the group consisting of hydrogen, a substituted or unsubstituted alkyl group, and a substituted or unsubstituted aromatic group);

$R_1$ to $R_3$ are each a substituted or unsubstituted aromatic group or a substituted or unsubstituted heterocyclic aromatic group with a proviso that $X_1$ to $X_3$ be a substituted or unsubstituted benzene ring; and $R_1$ to $R_3$ each are selected from the group consisting of hydrogen, a substituted or unsubstituted alkyl group, a substituted or unsubstituted aromatic group, and a substituted or unsubstituted heterocyclic aromatic group with a proviso that $X_1$ to $X_3$ be a substituted or unsubstituted 5-membered heterocyclic aromatic group.

2. The compound as set forth in claim 1, wherein the compound of Formula 1 is a compound of Formula 2:

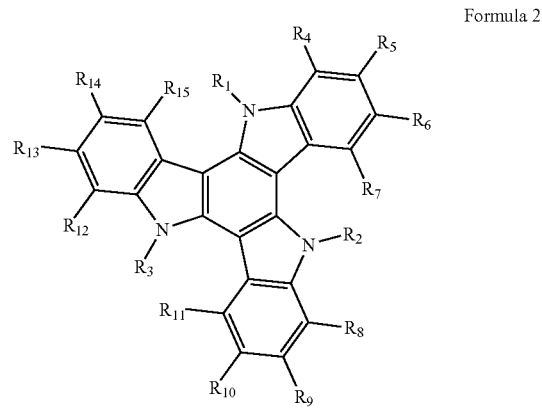

Formula 2 wherein, $R_1$ to $R_3$ each are a substituted or unsubstituted aromatic group, or a substituted or unsubstituted heteroaromatic group; and $R_4$ to $R_{15}$ are each selected from the group consisting of hydrogen, a halogen atom, a nitrile group (CN), a nitro group ($NO_2$), a formyl group, an acetyl group, a benzoyl group, an amide group, a styryl group, an acetylene group, a quinoline group, a quinazoline group, a phenanthroline group, a cuproin group, a substituted or unsubstituted alkyl group, a substituted or unsubstituted aromatic group, a substituted or unsubstituted aralkyl group, a substituted or unsubstituted arylamine group, a substituted or unsubstituted alkylamine group, a substituted or unsubstituted aralkylamine group, and a substituted or unsubstituted heterocyclic group.

3. The compound as set forth in claim 1, wherein the compound of Formula 1 is a compound of Formula 3:

Formula 3

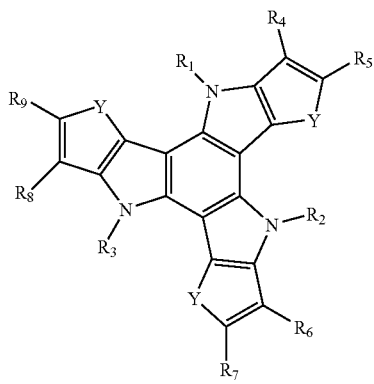

wherein,
$R_1$ to $R_3$ each are selected from the group consisting of hydrogen, a substituted or unsubstituted alkyl group, a substituted or unsubstituted aromatic group, and a substituted or unsubstituted heterocyclic aromatic group;

$R_4$ to $R_9$ each are selected from the group consisting of hydrogen, a halogen atom, a nitrile group (CN), a nitro group ($NO_2$), a formyl group, an acetyl group, a benzoyl group, an amide group, a styryl group, an acetylene group, a quinoline group, a quinazoline group, a phenanthroline group, a cuproin group, a substituted or unsubstituted alkyl group, a substituted or unsubstituted aromatic group, a substituted or unsubstituted aralkyl group, a substituted or unsubstituted arylamine group, a substituted or unsubstituted alkylamine group, a substituted or unsubstituted aralkylamine group, and a substituted or unsubstituted heterocyclic group; and Y is selected from the group consisting of O, S, and NR' (R' is selected from the group consisting of hydrogen, a substituted or unsubstituted alkyl group, and a substituted or unsubstituted aromatic group).

4. An organic light emitting device, comprising:
a first electrode;
one or more organic material layers including a light emitting layer; and
a second electrode,
wherein said first electrode, the one or more organic material layers, and the second electrode are sequentially layered, and the one or more organic material layers include the compound according to Formula 1:

Formula 1

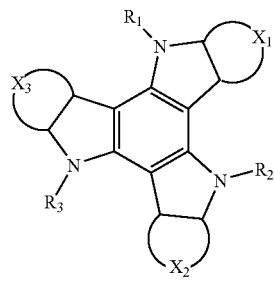

wherein,
$X_1$ to $X_3$ each are a substituted or unsubstituted benzene ring, or a substituted or unsubstituted 5-membered heterocylic aromatic group which includes a ring member selected from the group consisting of O, S, and NR' (R' is selected from the group consisting of hydrogen, a substituted or unsubstituted alkyl group, and a substituted or unsubstituted aromatic group);

R1 to R3 are each a substituted or unsubstituted aromatic group or a substituted or unsubstituted heterocyclic aromatic group with a proviso that $X_1$ to $X_3$ be a substituted or unsubstituted benzene ring; and $R_1$ to $R_3$ each are selected from the group consisting of hydrogen, a substituted or unsubstituted alkyl group, a substituted or unsubstituted aromatic group, and a substituted or unsubstituted heterocyclic aromatic group with a proviso that $X_1$ to $X_3$ be a substituted or unsubstituted 5-membered heterocyclic aromatic group.

5. The organic light emitting device as set forth in claim 4, wherein the light emitting layer of the organic material layers includes the compound according to Formula 1.

6. The organic light emitting device as set forth in claim 4, wherein the organic material layers comprise a hole injection layer, and the hole injection layer includes the compound according to Formula 1.

7. The organic light emitting device as set forth in claim 4, wherein the organic material layers comprise a hole transport layer, and the hole transport layer includes the compound according to Formula 1.

8. The organic light emitting device as set forth in claim 4, wherein the organic material layers comprise a layer which both injects and transports holes and which includes the compound according to Formula 1.

* * * * *